United States Patent
Nishimura et al.

(10) Patent No.: US 11,889,829 B2
(45) Date of Patent: Feb. 6, 2024

(54) MAMMALIAN CELL CRYOPRESERVATION LIQUID

(71) Applicant: OTSUKA PHARMACEUTICAL FACTORY, INC., Tokushima (JP)

(72) Inventors: Masuhiro Nishimura, Tokushima (JP); Natsuki Watanabe, Tokushima (JP); Yasutaka Fujita, Tokushima (JP); Tamaki Wada, Tokushima (JP)

(73) Assignee: OTSUKA PHARMACEUTICAL FACTORY, INC., Tokushima (JP)

( * ) Notice: Subject to any disclaimer, the term of this patent is extended or adjusted under 35 U.S.C. 154(b) by 193 days.

(21) Appl. No.: 16/468,773

(22) PCT Filed: Nov. 8, 2017

(86) PCT No.: PCT/JP2017/040272
§ 371 (c)(1),
(2) Date: Jun. 12, 2019

(87) PCT Pub. No.: WO2018/110159
PCT Pub. Date: Jun. 21, 2018

(65) Prior Publication Data
US 2020/0077643 A1 Mar. 12, 2020

(30) Foreign Application Priority Data
Dec. 14, 2016 (JP) ................................ 2016-242200

(51) Int. Cl.
*A01N 1/02* (2006.01)
*C12N 5/0775* (2010.01)

(52) U.S. Cl.
CPC ......... *A01N 1/0221* (2013.01); *A01N 1/0284* (2013.01); *C12N 5/0667* (2013.01)

(58) Field of Classification Search
CPC ................ A01N 1/0221; A01N 1/0284; C12N 5/0667
See application file for complete search history.

(56) References Cited

U.S. PATENT DOCUMENTS

| | | | |
|---|---|---|---|
| 9,943,075 B2 * | 4/2018 | Ho | A01N 1/0226 |
| 2005/0026133 A1 | 2/2005 | Nakatsuji et al. | |
| 2015/0320031 A1 * | 11/2015 | Andreasen | A01N 1/0221 435/1.3 |
| 2016/0120170 A1 | 5/2016 | Nishimura et al. | |

FOREIGN PATENT DOCUMENTS

| | | | |
|---|---|---|---|
| CA | 2089336 | 8/1993 | |
| CN | 105076116 | 11/2015 | |
| EP | 2330889 A0 | 6/2011 | |
| EP | 3 680 324 A1 | 7/2020 | |
| JP | 6-46840 | 2/1994 | |
| JP | 7-255469 | 10/1995 | |
| JP | 8-325101 | 12/1996 | |
| JP | 11-9270 | 1/1999 | |
| JP | 2002-233356 | 8/2002 | |
| JP | 2010-506563 | 3/2010 | |
| JP | 2015-526088 | 9/2015 | |
| JP | 2016-501873 | 1/2016 | |
| JP | 2016-34279 | 3/2016 | |
| WO | 2003/064634 | 7/2003 | |
| WO | 2005/108559 A2 | 11/2005 | |
| WO | WO-2007120829 A2 * | 10/2007 | ............ A01N 1/02 |
| WO | 2008/045498 | 4/2008 | |
| WO | 2010/021714 A2 | 2/2010 | |
| WO | 2010/021714 A3 | 2/2010 | |
| WO | 2014/028453 | 2/2014 | |
| WO | 2014/083169 | 6/2014 | |
| WO | WO-2014208053 A1 * | 12/2014 | ............ A01N 1/02 |
| WO | WO-2016063208 A1 * | 4/2016 | ......... A01N 1/0221 |
| WO | 2019/049957 A1 | 3/2019 | |

OTHER PUBLICATIONS

Atouf F. Cell-Based Therapies Formulations: Unintended components. AAPS J. Jul. 2016; 18(4):844-8. (Year: 2016).*
Eaker S, Armant M, Brandwein H, et al. Concise review: guidance in developing commercializable autologous/patient-specific cell therapy manufacturing. Stem Cells Transl Med. 2013;2(11):871-883 (Year: 2013).*
Al-Saqi SH, Saliem M, Quezada HC, Ekblad Å, Jonasson AF, Hovatta O, Götherström C. Defined serum- and xeno-free cryopreservation of mesenchymal stem cells. Cell Tissue Bank. Jun. 2015; 16(2):181-93. Epub Aug. 14, 2014 (Year: 2015).*
Al-Saqi et al., Defined serum- and xeno-free cryopreservation of mesenchymal stem cells. Cell and Tissue Banking 16 181-193 (2015). (Year: 2015).*
Naaldijk et al., Cryopreservation of Human Umbilical cord-derived mesenchymal stem cells in complex sugar based cryoprotective solutions. Journal of Biotechnology Letters, vol. 4, No. 2 (2013) pp. 95-99 (Year: 2013).*
Pollock et al., Combinations of osmolytes, including monosaccharides, disaccharides, and sugar alcohols act in concert during cryopreservation to improve mesenchymal stromal cell survival. Tissue Engineering Part C:Methods, vol. 22, No. 11 (Nov. 1, 2016) pp. 999-1008 (Year: 2016).*
J. R. Dobrinsky, "Cellular approach to cryopreservation of embryos," Theriogenology, 45, 1996, pp. 17-26.
Y. S. Ha et al., "Cryopreservation of human embryonic stem cells without theuse of a programmable freezer," Human Reprod., 20, 2005, pp. 1779-1785.
F. Holm et al., "An effective serum- and xeno-free chemically defined freezing procedure for human embryonic and induced pluripotent stem cells," Human Reprod., 25, 2010, pp. 1271-1279.

(Continued)

Primary Examiner — Kara D Johnson
(74) Attorney, Agent, or Firm — GREENBLUM & BERNSTEIN, P.L.C.

(57) ABSTRACT

A liquid for cryopreserving a cell and a liquid for administration of a mammalian cell capable of cryopreserving a mammalian cell and effectively suppressing cell death after thawing, and a method for cryopreserving a mammalian cell using the cell cryopreservation liquid. The liquid is an isotonic solution that includes 2.0 to 6.0% (w/v) of trehalose or a derivative thereof, or a salt of the trehalose or the derivative, 4.0 to 7.0% (w/v) of dextran or a derivative thereof, or a salt of the dextran or the derivative, and DMSO or glycerin.

7 Claims, No Drawings

(56) References Cited

OTHER PUBLICATIONS

Thermo Fisher Scientific, <http://www.learningatthebench.com/freezing-and-thawing-of-cells.html>, non-official translation ("Cryopreservation and defrost method of mammalian cells", "Cryopreservation method of mamalian cells"), Learning at the Bench, 2015 (with Manual translation in English).

Morishita et al., ""Effect of freezing medium supplemented with trehalose on improvement of cell viability after cryopreservation", Tissue culture research communications : the journal of experimental & applied cell culture research), vol. 26, No. 1", 2007, pp. 78 (with Manual translation in English).

"Stem-Cellbanker GMP grade, <http://www.zenoaq.jp/cellbanker/ja/pdf/msds_stem_cellbanker_gmp_grade_20150915ja.pdf>, non-official translation (Products safety datasheet)", Zenoaq Resource Co., Ltd., Sep. 15, 2015 (indicated as an "A" reference on the International Search Report in International Patent Application No. PCT/JP2017/040272, dated Feb. 6, 2018).

International Search Report issued in International Patent Application No. PCT/JP2017/040272, dated Feb. 6, 2018.

International Preliminary Report on Patentability with respect to International Patent Application No. PCT/JP2017/040272, dated Jun. 18, 2019.

Shu Z. et al., "Hematopoietic SCT with cryopreserved grafts: adverse reactions after transplantation and cryoprotectant removal before infusion", Bone Marrow Transplant., 2014, vol. 49, pp. 469-476.

Dimethylsulfoxide, vol. 7 of the Environmental Risk Assessment of Chemical Substances [Mar. 2009, online], https:/www.env.go.jp/chemi/report/h21-01/pdf/chpt1/1-2-2-12.pdf [retrieved on Apr. 11, 2019] (with concise explanation of releveance).

Chen et al., "Evaluation Report on Large-scale Mesenchymal Stem Cell Culture Technology", Chin. Med. Biotechnol., 8(4): 274-284 (2013). [w/ partial translation].

\* cited by examiner

MAMMALIAN CELL CRYOPRESERVATION LIQUID

TECHNICAL FIELD

The present invention relates to a liquid for cryopreserving a mammalian cell or a liquid for administration of a mammalian cell, consisting of an isotonic solution comprising: 2.0 to 6.0% (w/v) of trehalose or a derivative thereof, or a salt of the trehalose or the derivative (hereinafter sometimes referred to as "trehalose group"), 4.0 to 7.0% (w/v) of dextran or a derivative thereof, or a salt of the dextran or the derivative (hereinafter sometimes referred to as "dextran group"), and dimethyl sulfoxide (hereinafter referred to as "DMSO") or glycerin (glycerol), and a method for cryopreserving a mammalian cell comprising a step of cryopreserving a mammalian cell in such a mammalian cell cryopreservation liquid.

BACKGROUND ART

Cryopreservation of cells has been widely used as an essential technology in cell biology research. In recent years, the cell cryopreservation technology has been applied not only to the preservation of various established cell lines in cell banks all over the world, but also to the preservation of species in the livestock industry, the cryopreservation of sperm, eggs or fertilized eggs for increased production of livestock, and to the cryopreservation of germ cells in reproductive medicine, and the like.

Pluripotent stem cells such as embryonic stem cells (ES cells) and induced pluripotent stem cells (iPS cells) are cells having unlimited proliferation ability and multipotency to various tissue cells. Human pluripotent stem cells are expected to be applied to regenerative medicine by utilizing their properties, and in order to realize this, the establishment of a high-quality cell freezing technology, that is, a cell freezing technology guaranteeing high cell survival rate and undifferentiated ability after thawing, is essential.

Methods for cryopreserving cells are generally classified roughly into slow freezing methods and rapid freezing methods (vitrification method). A slow freezing method is a method of suspending cells in a cryopreservation liquid (Patent Documents 1 to 5) containing glycerin, DMSO, keratin hydrolyzate, hydrolyzed gelatin, serum, serum albumin, and the like as a cryoprotectant, and gradually freezing by lowering the temperature to about 1° C. per minute. By slowly cooling, intracellular water molecules are replaced with the cryoprotectant and dehydrated, the growth of ice crystals in and around cells is suppressed, and damage to the cell membranes and cell structures, and protein degeneration and cleavage is prevented (Non-patent Document 1). Recently, except when cryopreserving embryos, when cryopreserving general cells, it has been found that it is possible to freeze slowly using a box of polystyrene foam or a commercially available cell freezing box without strictly controlling the temperature adjustment using a program freezer. Since such a method is simple, it is also called a simple slow freezing method, and is widely used in laboratories, cell banks and the like.

On the other hand, the vitrification method is a method of freezing in a glassy state by rapid cooling in order to suppress the formation of ice crystals inside and outside the cells due to freezing. The vitrification method took a long time to be developed to practical application after being reported in 1937, but in 1985, a method using a vitrifying preservation liquid containing a cryoprotectant consisting of high concentrations of DMSO, acetamide, propylene glycol and polyethylene glycol, was developed. The development of this method has made possible the cryopreservation of mouse early embryos, and the cryopreservation of bovine embryos and porcine embryos, which were difficult with slow freezing methods. At present, the vitrification method is used in many institutions including embryo banks.

Recently, development of cryopreservation liquids for human ES cells and iPS cells, and improvement of cryopreservation methods have been actively carried out. For example, it has been disclosed that the cell survival rate after thawing is increased when human ES cells are suspended in a cryopreservation liquid containing 5% DMSO, 10% fetal bovine serum (FBS), and 10% ethylene glycol (EG), and cryopreserved using a simple slow freezing method (Non-patent Document 2). In addition, it has been disclosed that the cell survival rate after thawing is increased when human ES cells or iPS cells are suspended in a cryopreservation liquid (STEM-CELL BANKER [manufactured by Nippon Zenyaku Kogyo Co., Ltd.]) and cryopreserved using a simple slow freezing method (Non-Patent Document 3).

PRIOR ART DOCUMENTS

Patent Documents

Patent Document 1: International Publication No. WO 2003/064634 pamphlet
Patent Document 2: Japanese unexamined Patent Application Publication No. H6-46840
Patent Document 3: Japanese unexamined Patent Application Publication No. H7-255469
Patent Document 4: Japanese unexamined Patent Application Publication No. H8-325101
Patent Document 5: Japanese unexamined Patent Application Publication No. 2002-233356

Non-patent Documents

Non-patent Document 1: J. R. Dobrinsky, Theriogenology, 45, 17-26 (1996)
Non-patent Document 2: Y. S. Ha et al., Human Reprod., 20, 1779-1785 (2005)
Non-patent Document 3: F. Holm et al., Human Reprod., 25, 1271-1279 (2010)

SUMMARY OF THE INVENTION

Object to be Solved by the Invention

An object of the present invention is to provide a liquid for cryopreserving a cell and a liquid for administration of a mammalian cell capable of cryopreserving a mammalian cell and effectively suppressing cell death after thawing, and a method for cryopreserving a mammalian cell using the cell cryopreservation liquid.

Means to Solve the Object

In the course of intensive research to solve the above object, the present inventors have found that cell death after thawing can be suppressed more effectively than with prior-art mammalian cell cryopreservation liquids when mammalian cells are cryopreserved in a solution in which DMSO or glycerin is added and furthermore trehalose group and dextran group are added to be 2.0 to 6.0% (w/v) and 4.0 to 7.0% (w/v) respectively to an isotonic solution, and completed the present invention.

That is, the present invention is as follows.

[1] A liquid for cryopreserving a mammalian cell, consisting of an isotonic solution comprising: 2.0 to 6.0% (w/v) of trehalose or a derivative thereof, or a salt of the trehalose or the derivative, 4.0 to 7.0% (w/v) of dextran or a derivative thereof, or a salt of the dextran or the derivative, and DMSO or glycerin.

[2] The liquid for cryopreserving a mammalian cell according to [1], wherein the mammalian cell is a mammalian mesenchymal stem cell.

[3] The liquid for cryopreserving a mammalian cell according to [2], wherein the mammalian mesenchymal stem cell is a human adipose mesenchymal stem cell.

[4] The liquid for cryopreserving a mammalian cell according to any one of [1] to [3], wherein DMSO or glycerin is 1.0 to 15% (v/v) of DMSO.

[5] The liquid for cryopreserving a mammalian cell according to any one of [1] to [4], wherein the isotonic solution is a lactated Ringer's solution.

[6] A liquid for administration of a mammalian cell, consisting of the liquid for cryopreserving a mammalian cell according to any one of [1] to [5].

[7] The liquid for administration of a mammalian cell according to [6], wherein the mammalian cell is a mammalian mesenchymal stem cell.

[8] The liquid for administration of a mammalian cell according to [7], wherein the mammalian mesenchymal stem cell is a human adipose mesenchymal stem cell.

[9] A method for cryopreserving a mammalian cell, comprising a step of cryopreserving a mammalian cell in the liquid for cryopreserving a mammalian cell according to any one of [1] to [5].

[10] The method according to [9], wherein the mammalian cell is a mammalian mesenchymal stem cell.

[11] The method according to [10], wherein the mammalian mesenchymal stem cell is a human adipose mesenchymal stem cell.

Other embodiments of the present invention include the use of a combination of trehalose group, dextran group, DMSO or glycerin, and an isotonic solution to cryopreserve mammalian cells, or the use of a combination of trehalose group, dextran group, DMSO or glycerin, and an isotonic solution to prepare a liquid for cryopreserving a mammalian cell.

Effect of the Invention

According to the present invention, a good transplantable cell-containing liquid in regenerative medicine can be provided, since cell death when thawing cryopreserved mammalian cells can be suppressed more effectively than with prior-art liquids for cryopreserving a mammalian cell.

MODE OF CARRYING OUT THE INVENTION

The liquids for cryopreserving a mammalian cell of the present invention is a liquid consisting of an isotonic solution comprising trehalose group, dextran group and DMSO and/or glycerin (hereinafter sometimes referred to as "the present cryopreservation liquid"), that is limited to the use "for cryopreservation of a mammalian cell."

The above isotonic solution is not particularly limited as long as it is an isotonic solution in which the salt concentration, sugar concentration and the like are adjusted by sodium ions, potassium ions, calcium ions and the like so as to be approximately the same as the osmotic pressure of body fluid or cell fluid, specific examples thereof include saline or saline having a buffering effect (Phosphate buffered saline [PBS], Tris buffered saline [TBS], HEPES buffered saline, etc.), a Ringer's solution, a lactated Ringer's solution, an acetated Ringer's solution, a bicarbonated Ringer's solution, a 5% aqueous glucose solution, a basal medium for animal cell culture (DMEM, EMEM, RPMI-1640, α-MEM, F-12, F-10, M-199, etc.), an isotonic agent (glucose, D-sorbitol, D-mannitol, lactose, sodium chloride, etc.), and among these, lactated Ringer's solution is preferable. The isotonic solution may be one commercially available or may be prepared by oneself. Examples of commercially available products include Otsuka Dietary Injection (manufactured by Otsuka Pharmaceutical Factory, Inc.) (saline solution), Ringer's solution "Otsuka" (manufactured by Otsuka Pharmaceutical Factory, Inc.) (Ringer's solution), Lactec (registered trademark) injection (manufactured by Otsuka Pharmaceutical Factory, Inc.) (Lactated Ringer's solution), Lactated Ringer's solution "KS" (manufactured by Kyoritsu Pharmaceutical Co., Ltd.) (Lactated Ringer's Solution), Veen F Injection (manufactured by Kowa Pharmaceutical Co., Ltd.) (Acetated Ringer's Solution), Otsuka Glucose Injection 5% (manufactured by Otsuka Pharmaceutical Factory, Inc.) (5% aqueous glucose solution) and Bicanate Injection (manufactured by Otsuka Pharmaceutical Factory, Inc.) (Bicarbonated Ringer's solution). In the present description, "isotonic" means that the osmotic pressure is in the range of 250 to 380 mOsm/L.

Examples of the trehalose in the above-mentioned trehalose group include an α,α-trehalose, which is a disaccharide in which two α-glucoses are linked by a 1,1-glycosidic bond, but also an α,β-trehalose, which is a disaccharide in which an α-glucose and a β-glucose are linked by a 1,1-glycosidic bond, and a β,β-trehalose, which is disaccharide in which two β-glucoses are linked by a 1,1-glycosidic bond, but among these α,α-trehalose is preferable. These trehaloses can be produced by any known method such as chemical synthesis, production by microorganisms and production by enzymes, but commercial products can also be used. Examples of commercial products include α,α-trehalose (manufactured by Hayashibara Co., Ltd.) and α,α-trehalose (manufactured by Wako Pure Chemical Industries, Ltd.).

The trehalose derivative in the above-mentioned trehalose group is not particularly limited as long as it is a glycosyl trehalose in which one or more sugar units are linked to a disaccharide trehalose, and the glucosyl trehalose includes glucosyl trehalose, maltosyl trehalose and maltotriosyl trehalose.

Examples of the salt of trehalose and derivatives thereof in the above-mentioned trehalose group include an acid addition salt such as a hydrochloride, a hydrobromide, a hydroiodide, a phosphate, a nitrate, a sulfate, an acetate, a propionate, a toluene sulfonate, a succinate, an oxalate, a lactate, a tartrate, a glycolate, a methanesulfonate, a butyrate, a valerate, a citrate, a fumarate, a maleate and a malate, a metal salt such as a sodium salt, a potassium salt and a calcium salt, an ammonium salt and an alkyl ammonium salt. These salts are used as a solution at the time of use, and those having the same effect as trehalose are preferable. These salts may form a hydrate or a solvate, and any of them can be used alone or in combination of two or more as appropriate.

The dextran in the above-mentioned dextran group is not particularly limited as long as it is a polysaccharide consisting of D-glucose $(C_6H_{10}O_5)_n$ and has an α1→6 bond as the main chain, and examples of the weight-average molecular weight (Mw) of dextran include dextran 40 (Mw=40000) and dextran 70 (Mw=70000). These dextrans can be produced by any known method such as chemical synthesis, production by microorganisms and production by enzymes, but commercial products can also be used. Examples of commercial products include Dextran 40 (manufactured by Tokyo Chemical Industry Co., Ltd.) and Dextran 70 (manufactured by Tokyo Chemical Industry Co., Ltd.).

The dextran derivatives in the above-mentioned dextran group include dextran sulfate, carboxylated dextran, diethylaminoethyl (DEAE)-dextran and the like.

Examples of the salt of dextran and derivatives thereof in the above-mentioned dextran group include an acid addition salt such as a hydrochloride, a hydrobromide, a hydroiodide, a phosphate, a nitrate, a sulfate, an acetate, a propionate, a toluene sulfonate, a succinate, an oxalate, a lactate, a tartrate, a glycolate, a methanesulfonate, a butyrate, a valerate, a citrate, a fumarate, a maleate and a malate, a metal salt such as a sodium salt, a potassium salt and a calcium salt, an ammonium salt and an alkyl ammonium salt. These salts are used as a solution at the time of use, and those having the same effect as dextran are preferable. These salts may form a hydrate or a solvate, and any of them can be used alone or in combination of two or more as appropriate.

The concentration of trehalose group in the present cryopreservation liquid may be in the range of 2.0 to 6.0% (w/v), with examples including 2.0 to 5.6% (w/v), 2.0 to 5.2% (w/v), 2.0 to 4.8% (w/v), 2.0 to 4.4% (w/v), 2.0 to 4.0% (w/v), 2.0 to 3.6% (w/v), 2.0 to 3.2% (w/v), 2.0 to 3.0% (w/v), 2.4 to 6.0% (w/v), 2.8 to 6.0% (w/v), 3.2 to 6.0% (w/v), 3.6 to 6.0% (w/v), 4.0 to 6.0% (w/v), 4.4 to 6.0% (w/v), 4.8 to 6.0% (w/v), 5.0 to 6.0% (w/v), 2.4 to 6.0% (w/v), 2.4 to 5.6% (w/v), 2.4 to 5.2% (w/v), 2.4 to 4.8% (w/v), 2.4 to 4.4% (w/v), 2.4 to 4.0% (w/v), 2.4 to 3.6% (w/v), 2.4 to 3.2% (w/v) and 2.4 to 3.0% (w/v), and 2.4 to 3.0% (w/v) being preferable.

The concentration of dextran group in the present cryopreservation liquid may be in the range of 4.0 to 7.0% (w/v), with examples including 4.0 to 6.6% (w/v), 4.0 to 6.2% (w/v), 4.0 to 5.8% (w/v), 4.0 to 5.4% (w/v), 4.0 to 5.0% (w/v), 4.4 to 7.0% (w/v), 4.8 to 7.0% (w/v), 5.2 to 7.0% (w/v), 5.6 to 7.0% (w/v), 6.0 to 7.0% (w/v), and 4.0 to 5.0% (w/v) being preferable.

The concentration of DMSO in the present cryopreservation liquid is usually 0.1% (v/v) or more, preferably 0.3% (v/v) or more, more preferably 0.6% (v/v) or more and further preferably 1.0% (v/v) or more, and from the viewpoint of avoiding cytotoxicity, it is usually 30% (v/v) or less, preferably 25% (v/v) or less, more preferably 20% (v/v) or less and further preferably 15% (v/v) or less. Therefore, the concentration of DMSO in the present cryopreservation liquid is usually in the range of 0.1 to 30% (v/v), preferably 0.3 to 25% (v/v), more preferably 0.6 to 20% (v/v) and further preferably 1.0 to 15% (v/v). DMSO can be produced by chemical synthesis, but commercial products can also be used. Examples of commercial products include those manufactured by Wako Pure Chemical Industries, Ltd. and Nacalai Tesque Inc.

The concentration of glycerin in the present cryopreservation liquid is usually 0.1% (v/v) or more, preferably 0.3% (v/v) or more, more preferably 0.6% (v/v) or more and further preferably 1.0% (v/v) or more, and when considering the ease of preparation of the present cryopreservation liquid, it is usually 50% (v/v) or less, preferably 40% (v/v) or less, more preferably 30% (v/v) or less and further preferably 20% (v/v) or less. Therefore, the concentration of glycerin in the present cryopreservation liquid is usually in the range of 0.1 to 50% (v/v), preferably 0.3 to 45% (v/v), more preferably 0.6 to 30% (v/v) and further preferably 1.0 to 20% (v/v). Glycerin can be produced by chemical synthesis, but commercial products can also be used. Examples of commercial products include those manufactured by Wako Pure Chemical Industries, Ltd. and Nacalai Tesque Inc.

The present cryopreservation liquid contains trehalose group, dextran group, DMSO and/or glycerin (hereinafter sometimes collectively referred to as "the present cryoprotective components") as active components (cryoprotective components) to suppress cell death when cryopreserving and then thawing mammalian cells. The fact that the present cryopreservation liquid can suppress cell death when cryopreserving and then thawing mammalian cells can be confirmed using known methods capable of detecting cell death such as the Trypan Blue staining method, the TUNEL method, the Nexin method and the FLICA method.

Examples of optional components in the present cryopreservation liquid include a cryoprotective component other than the present cryoprotective components (for example, ethylene glycol, propylene glycol, polyethylene glycol, sericin, isomaltooligosaccharide), an isotonic agent (for example, glucose, D-sorbitol, D-mannitol, lactose, sodium chloride, etc.), a chelating agent (for example, EDTA, EGTA, citric acid, salicylate), a solubilizer, a preservative, an antioxidant and an amino acid (for example, proline, glutamine). "Optional component" in the present description means a component that may or may not be included.

In addition, the present cryopreservation liquid does not contain serum or serum-derived components derived from human, bovine and the like (for example, albumin).

The liquid for administration of a mammalian cell of the present invention is the present cryopreservation liquid limited to the use "for administration of a mammalian cell to a mammal", that is, an isotonic solution containing trehalose group, dextran group, DMSO and/or glycerin, which is limited to the use "for cryopreservation of a mammalian cell" and the use "for administration of a mammalian cell to a mammal". The present cryopreservation liquid (preferably, one containing little or no serum or serum-derived component as described above) does not adversely affect mammalian organisms, even if it is directly administered (for example, intravenously administered) to a mammalian organism. For this reason, the present cryopreservation liquid (preferably, one containing little or no serum or serum-derived component as described above) can be advantageously used as a liquid "for cryopreservation of mammalian cells and for administration (for example, intravenous administration) of a mammalian cell to a mammal after thawing."

The method for cryopreserving a mammalian cell according to the present invention is not particularly limited, as long as it comprises a step of cryopreserving a mammalian cell in the present cryopreservation liquid, that is, a step of cryopreserving the present cryopreservation liquid containing a mammalian cell, and it may be a slow freezing method or it may be a rapid freezing method (vitrification method). Examples of such slow freezing method include a method of freezing the present cryopreservation liquid containing mammalian cells in a low temperature freezer or an ultra low temperature freezer (usually in the range of −20° C. to −150° C.) and then preserving it in liquid nitrogen (usually in the range of −150° C. to −196° C.). Examples of the above rapid freezing method include a method of preserving mammalian cells by suspending them in the present cryopreservation liquid, then transferring them in a straw as necessary and rapidly freezing them in liquid nitrogen (usually in the range of −150° C. to −196° C.). Cell survival rate when mammalian cells are cryopreserved and then thawed may vary depending on the type of mammalian cell. For this reason, it is preferable to select a cryopreservation method with a higher cell survival rate after freezing and thawing depending on the cells to be cryopreserved.

Examples of the mammalian cells include, in addition to mammalian stem cells administered via blood vessels for regenerative medicine and the like, mammalian islet cells intravenously administered to type I diabetes patients, mammalian dendritic cells intravenously administered to cancer patients, natural killer cells, alpha beta ($\alpha\beta$) T cells, gamma delta ($\gamma\delta$) T cells and cytotoxic T lymphocytes (CTL). In the present description, examples of the mammal include a rodent such as a mouse, a rat, a hamster and a guinea pig, a lagomorph such as a rabbit, an ungulate such as a pig, a cow, a goat, a horse and a sheep, a carnivore such as a dog and a cat, and a primate such as a human, a monkey, a rhesus monkey, a cynomolgus monkey, a marmoset, an orangutan and a chimpanzee, and among these, suitable examples include a mouse, a pig and a human.

Moreover, the above-mentioned "stem cell" means an immature cell having self-replication ability and differentiation/proliferation ability. Stem cells include subpopulations of pluripotent stem cells, multipotent stem cells, unipotent stem cells, depending on their differentiation ability. A pluripotent stem cell means a cell which cannot be an individual per se, but has the ability to differentiate into all tissues and cells constituting a living body. A multipotent stem cell means a cell having the ability to differentiate into a plurality of types of tissues and cells, but not all types. A unipotent stem cell means a cell having the ability to differentiate into specific tissues or cells.

Examples of the pluripotent stem cell include an embryonic stem cell (ES cell), an EG cell and an iPS cell. ES cells can be produced by culturing inner cell mass on feeder cells or in a medium containing LIF. Methods for producing ES cells are described, for example, in WO 96/22362, WO 02/101057, U.S. Pat. Nos. 5,843,780, 6,200,806 and 6,280, 718. EG cells can be produced by culturing primordial germ cells in a medium containing mSCF, LIF and bFGF (Cell, 70: 841-847, 1992). iPS cells can be produced by introducing reprogramming factors such as Oct3/4, Sox2 and Klf4 (if necessary, also c-Myc or n-Myc) into somatic cells (for example, fibroblasts, skin cells) (Cell, 126: p. 663-676, 2006; Nature, 448: p. 313-317, 2007; Nat Biotechnol, 26; p. 101-106, 2008; Cell 131: p. 861-872, 2007; Science, 318: p. 1917-1920, 2007; Cell Stem Cells 1: p. 55-70, 2007; Nat Biotechnol, 25: p. 1177-1181, 2007; Nature, 448: p. 318-324, 2007; Cell Stem Cells 2: p. 10-12, 2008; Nature 451: p. 141-146, 2008; Science, 318: p. 1917-1920, 2007). In addition, stem cells established by culturing an initial embryo produced by nuclear transfer of somatic cell nuclei are also preferable as pluripotent stem cells (Nature, 385, 810 (1997); Science, 280, 1256 (1998); Nature Biotechnology, 17, 456 (1999); Nature, 394, 369 (1998); Nature Genetics, 22, 127 (1999); Proc. Natl. Acad. Sci. USA, 96, 14984 (1999)), Rideout III et al. (Nature Genetics, 24, 109 (2000)).

Example of the multipotent stem cell include a mesenchymal stem cell that can differentiate into cells such as adipocytes, osteocytes and chondrocytes; a hematopoietic stem cell that can differentiate into blood cells such as white blood cells, red blood cells and platelets; a neural stem cell that can differentiate into neurons, astrocytes, and oligodendrocytes; and a somatic stem cell such as a bone marrow stem cell and a germ stem cells. The pluripotent stem cells are preferably mesenchymal stem cells. A mesenchymal stem cell means a stem cell that can differentiate into all or some of the osteoblasts, chondroblasts and lipoblasts. Multipotent stem cells can be isolated from a living body by a known method per se. For example, mesenchymal stem cells can be collected from mammalian bone marrow, adipose tissue, peripheral blood, umbilical cord blood and the like by a known general method. In addition, human mesenchymal stem cells can be isolated by culture and passage of hematopoietic stem cells after bone marrow aspiration (Journal of Autoimmunity, 30 (2008) 163-171). Multipotent stem cells can also be obtained by culturing the above pluripotent stem cells under appropriate inducing conditions. The mesenchymal stem cell is preferably a mesenchymal stem cell derived from human adipose.

Examples of the mammalian cell preserved in the present cryopreservation liquid include adherent cells. In the present description, an "adherent" cell means an anchorage-dependent cell that can survive, proliferate, or produce substances by adhering to a scaffold. Examples of the adherent stem cell include a pluripotent stem cell, a mesenchymal stem cell, a neural stem cell, a bone marrow stem cell and a germ stem cell. The adherent stem cell is preferably a mesenchymal stem cell.

The mammalian cells (population) preserved in the present cryopreservation liquid may be separated from a living body or may be subcultured in vitro, but it is preferable that they be isolated or purified. In the present description, "isolation or purification" means that an operation which removes components other than the target components is performed. The purity of the isolated or purified mammalian cells (ratio of target cells such as the number of mammalian stem cells to the total cell number) is usually 30% or more, preferably 50% or more, more preferably 70% or more and further preferably 90% or more (for example, 100%).

It is preferable that the mammalian cells (population) preserved in the present cryopreservation liquid be in the state of single cells. In the present description, "the state of single cell" means that it does not form a mass by gathering with other cells (that is, a non-aggregated state). Mammalian cells in the state of single cell can be prepared by treating mammalian cells cultured in vitro with enzymes such as trypsin/EDTA and the like, and then suspending the cells by known methods in this technical field such as pipetting and tapping. The ratio of mammalian cells in the state of single cell contained in the mammalian cells is usually 70% or more, preferably 90% or more, more preferably 95% or more and further preferably 99% or more (for example, 100%). The ratio of cells in the state of single cell can be determined by investigating the presence or absence of aggregation of a plurality of randomly selected cells (for example, 1000 cells) by dispersing the mammalian cells in PBS and observing them under a microscope.

Hereinafter, the present invention will be more specifically described by examples, but the technical scope of the present invention is not limited to these examples. In the following examples, a lactated Ringer's solution containing 3% (w/v) trehalose and 5% (w/v) dextran 40 is sometimes referred to as "TDR solution" for convenience.

EXAMPLE 1

1. Confirmation that the Present Cryopreservation Liquid is Useful as a Mammalian Cell Cryopreservation Liquid In order to confirm that the present cryopreservation liquid is useful as a mammalian cell cryopreservation liquid, mammalian cells were cryopreserved in a mixture of DMSO or glycerin and TDR solution, and the cell survival rate after thawing was analyzed.

1-1 Materials and Methods

[Mammalian Cells]

For the test, the human adipose derived mesenchymal stem cells (hAD-MSC) listed in the following Table 1 were used.

TABLE 1

| | |
|---|---|
| Donor age, sex, origin | 38 years old, female, fat |
| Number of donors | 1 |
| Lot number | 0000421627 |
| Passage number at arrival | 1 |
| Preservation method | Preserved in liquid nitrogen |
| Supply source | Lonza Walkersville |
| Agency name | Lonza Japan |

[TDR Solution]

The TDR solution was prepared using trehalose (manufactured by Hayashibara Co., Ltd.), low-molecular-weight dextran L injection (10% [w/v] dextran-containing Lactec injection) (manufactured by Otsuka Pharmaceutical Factory, Inc.), and Lactec injection (manufactured by Otsuka Pharmaceutical Factory, Inc.).

[Culture of Mammalian Cells]

hAD-MSCs were cultured according to a standard method. That is, hAD-MSCs were placed in a 75 cm$^2$ flask to which ADSC-BM (Adipose Derived Stem Cell Basal Medium) (manufactured by Lonza Walkersville, PT-3273) containing human adipose derived stem cell addition factor set (manufactured by Lonza Walkersville, PT-4503) was added (hereinafter simply referred to as the "culture solution"), and subcultured in a CO2 incubator (at 37° C.). In addition, the replacement of the culture medium was performed every three days.

[Preparation and Freezing of Mammalian Cell-Containing Cryopreservation Liquid]

The preparation and freezing of the mammalian cell-containing cryopreservation liquid were performed according to the following procedures [1] to [12].

[1] A personal incubator was warmed to 37±2° C.

[2] The 75 cm$^2$ flasks culturing hAD-MSCs were removed from the CO$_2$ incubator.

[3] The condition of the cells was observed under an inverted microscope, and about 90% (80 to 100%) confluent was used.

[4] The culture solution was aspirated and 8 mL of PBS(−) was added to each 75 cm$^2$ flask.

[5] After aspirating PBS(−), 4 mL of trypsin/EDTA (CC-5012, manufactured by Lonza Walkersville) was added to each flask, and incubated in a personal incubator at 37±2° C. for 5 minutes.

[6] The cells were gently shaken while being observed under an inverted microscope until the cells were detached by about 90%.

[7] In order to stop the trypsin reaction, 8 mL each of trypsin neutralization solution (TNS; CC-5002, manufactured by Lonza Walkersville) was added, the cells were detached by pipetting, and transferred to a 50 mL conical tube.

[8] After centrifugal treatment (centrifuge setting conditions: 210×g, centrifugation time 5 minutes, 20° C.), the supernatant was removed, a fixed volume (2 mL per each cm$^2$ flask) of PBS(−) was added, and the cells were suspended.

[9] A portion (20 µL) of the cell suspension was separated, mixed with 20 µL of trypan blue staining solution (manufactured by Gibco), and the total cell number and dead cell number were measured with a cell counting board. The number of cells measured was the total number of cells in the area of a four corners cell counting chamber in one cell counting unit, using a cell counting board.

[10] A fixed amount of the remaining cell suspension was dispensed into each 15 mL ClariFind polypropylene conical tube using a fin pipette (100-1000 µL) and centrifuged at 210×g for 5 minutes at 25° C.

[11] The supernatant was removed and the cells were suspended in each cell cryopreservation liquid (TDR solution containing 0, 0.5, 1.0, 2.0, 5.0, or 10% (v/v) DMSO (manufactured by Wako Pure Chemical Industries, Ltd.) or 10% (v/v) glycerin (manufactured by Wako Pure Chemical Industries, Ltd.), or STEM-CELL BANKER [manufactured by Nippon Zenyaku Kogyo Co., Ltd.]) so as to be 3.0×10$^6$ cells/mL.

[12] 1 mL of each cell suspension was dispensed into dedicated vials and placed in a Bicell freezing container (manufactured by Nihon Freezer Co., Ltd.) to freeze the cells at -80° C. (3 hours or more), and then promptly transferred to a liquid nitrogen tank.

[Evaluation Method]

After freezing and thawing the mammalian cell-containing cryopreservation liquids, evaluation of the viable cell rate and cell proliferation rate was performed according to the following procedures [1] to [6].

[1] A thermostat was set to 37° C. and warmed.

[2] The culture solution was added to the number of 75 cm$^2$ flasks necessary for culture, and was allowed to stand for 30 minutes or more in a CO$_2$ incubator to be equilibrated.

[3] The vial containing the frozen cells was removed from the liquid nitrogen tank, quickly transferred to the thermostat set to 37° C., and thawed while lightly stirring.

[4] After gently stirring (pipetting 5 times) and suspending the cells, a portion (20 µL) was dispensed into 1.5 mL microtubes to which 20 µL of trypan blue staining solution had been previously added. The cell suspension mixed with trypan blue staining solution was collected on a cell counting plate, and the cell survival rate immediately after freezing and thawing (Table 2 [n=1] and Table 4 [n =3]) was calculated by counting the total cell number and the number of trypan blue positive cells (dead cells).

[5] The remaining cell suspension was used to seed in a 75 cm$^2$ flask containing a previously prepared culture solution so as to be 3.0×10$^6$ cells/mL and cultured in a CO$^2$ incubator. In addition, after allowing the partially remaining cell suspension to stand at 25° C. for 6 hours and 24 hours, the cell survival rate when frozen and thawed then allowed to stand at 25° C. for 6 hours and 24 hours (Table 5 [n=3] and Table 6 [n=3]) was calculated by counting the total cell number and the number of dead cells, according to the procedure [9] described in the above [Preparation and freezing of mammalian cell-containing cryopreservation liquid].

[6] On days 1, 3, 5, and 7 after culture, the cell proliferation rate when frozen and thawed then cultured for 1, 3, 5, and 7 days (Table 3 [n =2] and Table 7 [n =3]) was calculated by counting the total cell number after recovering the cells, according to the procedures [1] to [9] described in the above [Preparation and freezing of mammalian cell-containing cryopreservation liquid].

1-2 Results

First, the concentration of DMSO to be added to the TDR solution was examined. As a result, when cells were cryopreserved in a TDR solution containing 1.0 to 10% of DMSO, both cell survival rate (Table 2) and cell proliferation rate (Table 3) immediately after thawing were high. From these results, in the following experiment, the concentration of DMSO to be added to the TDR solution was fixed at 10%.

Next, a comparative experiment with STEM-CELL BANKER (manufactured by Nippon Zenyaku Kogyo Co., Ltd.), which is an existing cell cryopreservation liquid, was performed. As a result, the cell survival rate immediately after thawing when the cells were cryopreserved in TDR solution containing 10% DMSO, showed a value as high as that of with a STEM-CELL BANKER (Table 4). In addition, the cell survival rate when frozen and thawed then allowed to stand at 25° C. for 6 hours and 24 hours, was higher when cells were cryopreserved in a TDR solution containing 10% DMSO than when cells were cryopreserved in STEM-CELL BANKER (Tables 5 and 6). Furthermore, similar effects were obtained when using a cell cryopreservation liquid in which glycerin was added to the TDR solution instead of DMSO (Tables 5 and 6). After mixing DMSO or glycerin into the TDR solution, the trehalose concentration was 2.7% and the dextran concentration was 4.5%. On the other hand, the cell proliferation rate when the cells were cryopreserved in a TDR solution containing 10% DMSO or 10% glycerin, showed a value as high as that of with a STEM-CELL BANKER (Table 7).

The above results indicate that a proliferation rate comparable to when using an existing mammalian cell cryopreservation liquid (STEM-CELL BANKER) can be obtained when mammalian cells are cryopreserved in an isotonic solution containing approximately 2.7% (2.0 to 6.0%) of trehalose, approximately 4.5% (4.0 to 7.0%) of dextran, and DMSO or glycerin, and also that excellent effects can be obtained, such that the cell survival rate after freezing and thawing is higher than when using the existing mammalian cell cryopreservation liquid (STEM-CELL BANKER).

TABLE 2

| DMSO Concentration (%) | Survival rate (%) |
| --- | --- |
| 0 | 81 |
| 0.5 | 89 |
| 1.0 | 91 |
| 2.0 | 96 |
| 5.0 | 96 |
| 10 | 95 |

TABLE 3

| | | DMSO Concentration (%) | | | | | |
| --- | --- | --- | --- | --- | --- | --- | --- |
| | | 0 | 0.5 | 1.0 | 2.0 | 5.0 | 10 |
| Immediately after thawing | | 100 | 100 | 100 | 100 | 100 | 100 |
| Day 5 | First time | 260 | 270 | 395 | 346 | 389 | 294 |
| | Second time | 162 | 273 | 358 | 364 | 348 | 371 |
| | Mean | 211 | 272 | 376 | 355 | 369 | 332 |

The numerical values (cell number) in the table are shown as relative values when the number of cells immediately after (freezing and) thawing is set to 100 in cells preserved in each concentration of DMSO.

TABLE 4

| | STEM-CELLBANKER | TDR Solution containing 10% DMSO | TDR Solution containing 10% glycerin |
| --- | --- | --- | --- |
| First time | 89 | 99 | 97 |
| Second time | 96 | 97 | 98 |
| Third time | 93 | 97 | 94 |
| Mean | 93 | 98 | 97 |
| Standard deviation (SD) | 4 | 1 | 2 |

The numerical values in the table indicate the cell survival rate (%) immediately after freezing and thawing.

TABLE 5

| | STEM-CELLBANKER | TDR Solution containing 10% DMSO | TDR Solution containing 10% glycerin |
| --- | --- | --- | --- |
| First time | 82 | 98 | 98 |
| Second time | 88 | 98 | 99 |
| Third time | 92 | 95 | 96 |
| Mean | 87 | 97 | 97 |
| Standard deviation (SD) | 5 | 1 | 2 |

The numerical values in the table indicate the cell survival rate (%) after freezing and thawing then allowing to stand at 25° C. for 6 hours.

TABLE 6

| | STEM-CELLBANKER | TDR Solution containing 10% DMSO | TDR Solution containing 10% glycerin |
| --- | --- | --- | --- |
| First time | 81 | 96 | 93 |
| Second time | 82 | 94 | 91 |
| Third time | 86 | 95 | 95 |
| Mean | 83 | 95 | 93 |
| Standard deviation (SD) | 3 | 1 | 2 |

The numerical values in the table indicate the cell survival rate (%) after freezing and thawing then allowing to stand at 25° C. for 24 hours.

TABLE 7

| Cell Cryopreservation Liquid | At seeding | Day 1 | Day 3 | Day 5 | Day 7 |
|---|---|---|---|---|---|
| STEM-CELLBANKER | 100 | 121 ± 37 | 337 ± 50 | 504 ± 82 | 701 ± 117 |
| TDR Solution containing 10 DMSO | 100 | 137 ± 6 | 419 ± 81 | 568 ± 109 | 798 ± 125 |
| TDR Solution containing 10 glycerin | 100 | 98 ± 15 | 293 ± 22 | 398 ± 87 | 576 ± 59 |

The numerical values (cell number) in the table are shown as relative values when the number of cells at the time of seeding (immediately after freezing and thawing) is set to 100 in each cell cryopreservation liquid. Moreover, the values of day 1 to day 7 are mean values ±standard deviation (SD).

EXAMPLE 2

2. Examination of the Cryoprotective Effect by Combined use of Trehalose and Dextran, and of the Trehalose and Dextran Concentrations in the Mammalian Cell Cryopreservation Liquid In order to examine the cryoprotective effect by combined use of trehalose and dextran, and of the trehalose and dextran concentrations in the mammalian cell cryopreservation liquid, a mixture of a lactated Ringer's solution containing 3% of trehalose and 0 to 10% of dextran with 10% of DMSO (Table 8), and a mixture of lactated Ringer's solution containing 0 to 10% of trehalose and 5% of dextran with 10% of DMSO (Table 9) were prepared according to the method described in Example 1, and the hAD-MSCs were cryopreserved in these mixtures and cell survival rate after thawing (Tables 8 and 9) was calculated.

As a result, it was shown that the cell survival rate after freezing and thawing is higher when trehalose and dextran are used in combination, compared to when trehalose or dextran is used alone. In addition, when the concentrations of trehalose and dextran were respectively at least 0.9%, i.t was shown that 90% or more of the cells survived (Tables 8 and 9).

TABLE 8

| Trehalose concentration | Dextran concentration | Survival rate |
|---|---|---|
| 3.0 (2.7) | 0 (0) | 83.8 ± 4.0 |
| | 0.5 (0.45) | 87.3 ± 1.4 |
| | 1.0 (0.9) | 91.0 ± 3.0 |
| | 3.0 (2.7) | 93.8 ± 1.5 |
| | 5.0 (4.5) | 91.2 ± 3.4 |
| | 7.0 (6.3) | 93.7 ± 3.5 |
| | 10 (9.0) | 96.4 ± 2.7 |

The trehalose and dextran concentrations in the table indicate the concentration (%) prior to DMSO mixing, and the concentration (%) after DMSO mixing are indicated in parentheses. In addition, the survival rate in the table indicates the cell survival rate immediately after freezing and thawing (mean±standard deviation [SD], n=3) (%).

TABLE 9

| Dextran concentration | Trehalose concentration | Survival rate |
|---|---|---|
| 5.0 (4.5) | 0 (0) | 85.3 ± 3.7 |
| | 0.5 (0.45) | 83.9 ± 5.6 |
| | 1.0 (0.9) | 90.1 ± 6.7 |
| | 3.0 (2.7) | 96.5 ± 1.4 |
| | 5.0 (4.5) | 94.9 ± 1.3 |
| | 7.0 (6.3) | 94.3 ± 1.4 |
| | 10 (9.0) | 91.5 ± 2.5 |

The trehalose and dextran concentrations in the table indicate the concentration (%) prior to DMSO mixing, and the concentration (%) after DMSO mixing are indicated in parentheses. In addition, the survival rate in the table indicates the cell survival rate immediately after freezing and thawing (mean±standard deviation [SD], n=3) (%).

INDUSTRIAL APPLICABILITY

According to the present invention, since cell death when thawing cryopreserved mammalian cells can be effectively suppressed, it is useful in the field of transplantation medicine and the field of cancer treatment in regenerative medicine and the like.

The invention claimed is:

1. A liquid for cryopreserving a mammalian cell, consisting of an isotonic solution comprising: 2.0 to 6.0% (w/v) of trehalose or a trehalose derivative, or a salt of the trehalose or the trehalose derivative, 4.0 to 7.0% (w/v) of dextran or a dextran derivative, or a salt of the dextran or the dextran derivative, and 2.0 to 15% (v/v) of dimethylsulfoxide or glycerin, and not containing any of serum, albumin or glucose.

2. The liquid for cryopreserving a mammalian cell according to claim 1, wherein the concentration of dimethylsulfoxide in the liquid for cryopreserving a mammalian cell is 5.0 to 15% (v/v).

3. The liquid for cryopreserving a mammalian cell according to claim 2, wherein the isotonic solution is a lactated Ringer's solution.

4. The liquid for cryopreserving a mammalian cell according to claim 1, wherein the isotonic solution is a lactated Ringer's solution.

5. A method for cryopreserving a mammalian cell, comprising a step of cryopreserving a mammalian cell in the liquid for cryopreserving a mammalian cell according to claim 1.

6. The method according to claim 5, wherein the mammalian cell is a mammalian mesenchymal stem cell.

7. The method according to claim 6, wherein the mammalian mesenchymal stem cell is a human adipose mesenchymal stem cell.

* * * * *